US009959612B2

(12) United States Patent
Cauble et al.

(10) Patent No.: US 9,959,612 B2
(45) Date of Patent: May 1, 2018

(54) MEASURING OPTICAL TURBULENCE USING CELL COUNTING ALGORITHMS

(71) Applicants: Galen D. Cauble, San Diego, CA (US); David T. Wayne, San Diego, CA (US)

(72) Inventors: Galen D. Cauble, San Diego, CA (US); David T. Wayne, San Diego, CA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 42 days.

(21) Appl. No.: 15/252,345

(22) Filed: Aug. 31, 2016

(65) Prior Publication Data
US 2018/0061039 A1    Mar. 1, 2018

(51) Int. Cl.
| | |
|---|---|
| G06K 9/00 | (2006.01) |
| G06T 7/00 | (2017.01) |
| G06T 5/00 | (2006.01) |
| G01N 15/14 | (2006.01) |
| H04B 10/11 | (2013.01) |

(Continued)

(52) U.S. Cl.
CPC ....... *G06T 7/0004* (2013.01); *G01N 15/1463* (2013.01); *G06T 5/002* (2013.01); *G06T 7/0087* (2013.01); *H04B 10/07* (2013.01); *H04B 10/11* (2013.01); *G01N 2015/0065* (2013.01); *G01N 2015/1006* (2013.01); *G01N 2015/1465* (2013.01); *G01N 2015/1486* (2013.01); *G06T 2207/20148* (2013.01); *G06T 2207/30242* (2013.01)

(58) Field of Classification Search
CPC .............................. G06T 7/521; H04N 9/3161
See application file for complete search history.

(56) References Cited

U.S. PATENT DOCUMENTS

2010/0002743 A1* 1/2010 Markov ................ G01S 7/4814
372/96

FOREIGN PATENT DOCUMENTS

EP          0386927      *  9/1990  ............... A61B 3/12

OTHER PUBLICATIONS

Kostelec, P., "Basic cell counting and segmentation in Matlab" Internet: http://blog.pedro.si/2014/04/basic-cellsegmentation-in-matlab.htrnl, Apr. 2014 [Jun. 2015].

(Continued)

*Primary Examiner* — Eueng-Nan Yeh
(74) *Attorney, Agent, or Firm* — SSC Pacific Patent Office; Arthur K. Samora; Kyle Eppele (57) ABSTRACT

Methods for characterizing atmospheric turbulence along an optical path from a laser transmitter to a laser receiver can include the steps of counting the number of laser speckles at the receiver imaging plane, and then finding Fried's parameter $r_0$ using the counting result to characterize the turbulence along the path. Before counting speckles, images at the receiver image plane can be preprocessed by capturing the images. The captured images at the image plane can then be blurred and a threshold can be chosen so that only certain pixels in the image are further processed. The thresholding can be via Otsu's methods or via variants of a Gaussian fit. Kostelec's method can then be used to count speckles in the portions of the image that have made it through the thresholding step. Other counting methods could be used. Fried's can then be found using the speckle count.

20 Claims, 7 Drawing Sheets

(51) Int. Cl.
*H04B 10/07* (2013.01)
*G01N 15/10* (2006.01)
*G01N 15/00* (2006.01)

(56) References Cited

OTHER PUBLICATIONS

Al-Khazraji, B. K., et al., "An automated cell-counting algorithm for fluorescently-stained cells in migration assays". Biological Procedures Online, 13:9, Oct. 2011.
Hadjantonakis, A., and Papaioannou, V. E., "Dynamic in vivo imaging and cell tracking using ahistone fluorescent protein fusion in mice". BMC Biotechnology, 4:33, 2004, (published before this application Aug. 2016).
Cauble, Galen D. and Wayne, David T., "Blob Identification Algorithms Applied to Laser Speckle to Characterize Optical Turbulence", Proc. of SPIE, vol. 9614, 961403, 2015, (published before this application Aug. 2016).

\* cited by examiner

MEASURING OPTICAL TURBULENCE USING CELL COUNTING ALGORITHMS

FEDERALLY-SPONSORED RESEARCH AND DEVELOPMENT

The United States Government has ownership rights in this invention. Licensing inquiries may be directed to Office of Research and Technical Applications, Space and Naval Warfare Systems Center, Pacific, Code 72120, San Diego, Calif., 92152; telephone (619) 553-5118; email: ssc_pac_t2@navy.mil, referencing NC 104223.

FIELD OF THE INVENTION

The present invention pertains generally to methods for characterizing atmospheric turbulence. More specifically, the present invention pertains to methods for characterizing atmospheric turbulence along an optical path. The invention is particularly, but not exclusively, useful as methods for characterizing atmospheric turbulence along an optical path by counting laser speckles using interdisciplinary cell count theories from the life sciences.

BACKGROUND OF THE INVENTION

Atmospheric turbulence, or refractive-index fluctuations, along the path of a partially coherent beam can result in intensity fluctuations at the receiving end of the propagation path. At the pupil plane this phenomena can create a characteristic beam breakup, which can result in the appearance of "blobs" or "speckles" at the pupil plane, and which is referred to in this paper as "speckles", (as used herein, the term "speckles" is not to be confused with the speckle pattern created due to the scattering of a beam from a rough surface). These intensity fluctuations can severely limit the performance of free-space optical communication; thus, their characterization is of importance. One method of measuring atmospheric turbulence is by estimating Fried's coherence length, $r_0$, through its relationship with the number and size of discrete speckles captured on an image plane after propagation through a turbulent field.

In the medical fields, "blob" identification is becoming an important means of automating image analysis. These "blobs" can be representative of cells, bacteria, etc., in various types of images, and counting methods are able to count cells, detect blood vessel structures, map brain activity, and complete other manually tedious tasks. Considering the large effort put into optimizing these counting methods, these interdisciplinary counting techniques can be leveraged to quickly and effectively count speckles in an image from the receiver of a laser communications systems. The speckles can be due to atmospheric turbulence, and if the speckles can be counted, the atmospheric conditions can be characterized, which can allow for additional information such as maximum effective range of the communications system to be characterized.

In view of the above, it can be an object of the present invention to provide a method for characterizing atmospheric turbulence along an optical path without using a scintillometer. Another object of the present invention can be to provide a method for characterizing atmospheric turbulence along an optical path by adapting cell counting methods from the life sciences to count speckles along the optical path. Still another object of the present invention can be to provide a method for characterizing atmospheric turbulence along an optical path, in order to gage the coherency of a laser beam in the turbulence. Yet another object of the present invention to provide a method for characterizing atmospheric turbulence along an optical path that can be easy to accomplish and use in a cost-effective manner.

SUMMARY OF THE INVENTION

Methods for characterizing atmospheric turbulence along an optical path from a laser transmitter to a laser receiver can include the steps of counting the number of laser speckles at the receiver imaging plane, and then finding Fried's parameter $r_0$ using the counting result to characterize the turbulence along the path. To the count speckles, images at the receiver image plane can be captured. The captured images at the image plane can then be blurred and a threshold can be chosen so that only certain pixels in the image are further processed. The thresholding can be via Otsu's methods or via variants of a Gaussian fit. Kostelec's method can then be used to count the portions of the image that have made it through the thresholding step.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The novel features of the present invention will be best understood from the accompanying drawings, taken in conjunction with the accompanying description, in which similarly-referenced characters refer to similarly-referenced parts, and in which.

DETAILED DESCRIPTION OF THE EMBODIMENTS

In brief overview, laser beam speckle at an image plane resulting from atmospheric turbulence can contain information about the propagation channel. The number and size of the speckles can be used to infer the spatial coherence and thus the refractive index, $C_n^2$, along a path. The challenge with this technique is to be able to quickly and effect assess the rapidly evolving speckle pattern and non-uniformity of the speckle cell and count the speckles. To do this, the speckles in an image plane can be analogized to "blobs" on an image in the medical field, such as cells, bacteria, etc. Modern blob counting techniques used in biology, microscopy, and medical imaging can then be applied to turbulent speckle images, to estimate the number and size of the speckle cells, and algorithms which can use the automated counting algorithms can be generated to calculate path $C_n^2$ from speckle information and path geometry.

A. Fried's Coherence Length, $r_0$

As known in the optical prior arts, Fried's coherence length can be used to characterize the effects of atmospheric turbulence on an optical system. Primarily, it can describe system limitations on image resolution due to atmospheric conditions, and can be defined as the diameter over which the time-average wave front error does not exceed 1 radian. In the absence of atmosphere, an image formed at the focus of a telescope can have an angular resolution proportional to $\lambda/D$, where $\lambda$ is the wavelength of the source, and D is the aperture diameter of the receiving optics.

Fried's coherence length (when expressed in terms of refractive index structure constant, $c_n^2$, over a horizontal homogeneous path for a plane wave) can be given by Equation (1):

$$r_0 = [1.67 C_n^2 k^2 L]^{-\frac{2}{5}} \tag{1}$$

$$\text{Where } k = \frac{2\pi}{\lambda}$$

is the wave number and L is the path length from source to receiver.

B. Fried's Parameter and Speckle Patterns

The number of speckles in an image of the pupil plane of an image system can be related to the aperture size of the imaging system and $r_0$. We approximate the number of speckles by finding the ratio between the size of the seeing spot (the central spot of the diffraction pattern formed by interference of the wavefronts from the aperture) and the average size of a given speckle. As the resolution limit of the telescope under turbulence is limited by $r_0$, the size of the seeing spot is proportional to $$\left(\frac{\lambda}{r_0}\right)^2.$$

The separation of speckles is on the order of $$\frac{2\lambda}{D}$$

and thus their area is proportional to $$\left(\frac{2\lambda}{D}\right)^2.$$

Thus the number of speckles contained in the seeing spot can be given by Equation (2)

$$N = \left(\frac{\lambda}{r_0}\right)^2 \bigg/ \left(\frac{2\lambda}{D}\right)^2 = \left(\frac{D}{2r_0}\right)^2 \tag{2}$$

Where N is the number of speckles. This equation relates the number of speckles to a ratio between lens area of aperture diameter D and a seeing spot having a circle of diameter $\lambda/r_0$. Intuitively, the number of speckles can be proportional to how many $r_0$ "areas" can fit on the lens. By counting the number of speckles contained in the seeing spot one can calculate $r_0$, as indicated by Equation (3) below.

$$r_0 = \frac{D}{2}\sqrt{\frac{1}{N}} \tag{3}$$

Furthermore, the width of these speckles can be on the order of $r_0^3$.

From the above, it can be seen that if the number of speckles can be counted at the seeing spot within the lens area, then Fried's number can be determined. And once $r_0$ is determined, the atmospheric turbulence along the path of transmission of a coherent laser beam can be estimated, which can further allow the user to estimate the coherency (effectiveness) of the laser beam, based on the distance through the atmosphere, the laser beam must travel through.

C. Blob Counting

In order to count the speckles, counting methods from interdisciplinary fields can be used and adapted for the laser communications fields. For example, in the medical field, blobs identification and counting is becoming an important means of automating image analysis (as used herein, the term "blob" is used to define asymmetrical, non-uniform distinguishable variations within an image). Thus, counting methods are able to count cells, detect blood vessel structures, map brain activity, and complete other manually tedious tasks. These algorithms can use morphological operations to prepare the image and the watershed algorithm to segment the structures, and these interdisciplinary counting techniques can further be adapted for use in our counting speckles in turbulent speckled images, as described more fully below.

The speckle counting algorithms of the present invention can be based on two cell counting algorithms, a basic cell counting and segmentation algorithm described created by Pedro Kostelec and described in Kostelec, P., "Basic Cell Counting and Segmentation In Matlab" April 2014 (hereinafter, the Kostelec counting method). Alternatively a cell counting method used for counting stained cells in migration assays by Baraa K. Al-Khazraji and described in Al-Khazraji, B. K., et al., "An Automated Cell-Counting Algorithm For Fluorescently-Stained Cells In Migration Assays". Biological Procedures Online, 13:9, October 2011 (hereinafter, the Al-Khazraji counting method). The Kostelec and Al-Khazraji papers are hereby incorporated by reference herein.

Figure 1:
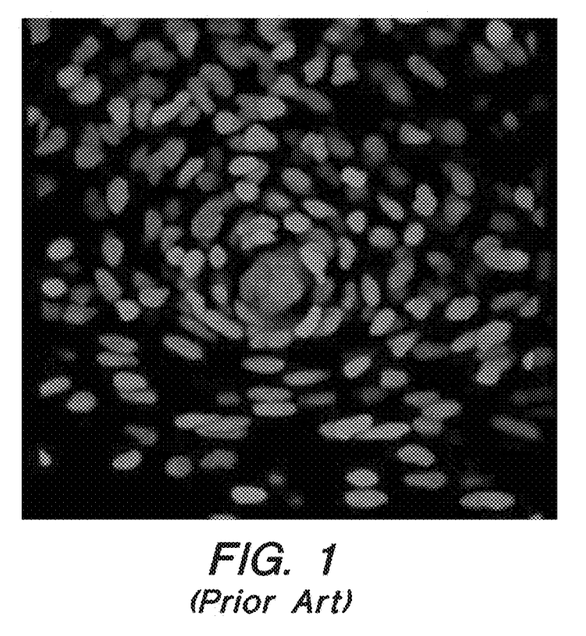
FIG. 1 is a color photograph of a prior art cell embryo from the medical field, with characteristic beam breakup blobs, prior to a counting method being applied.
Figure 2:
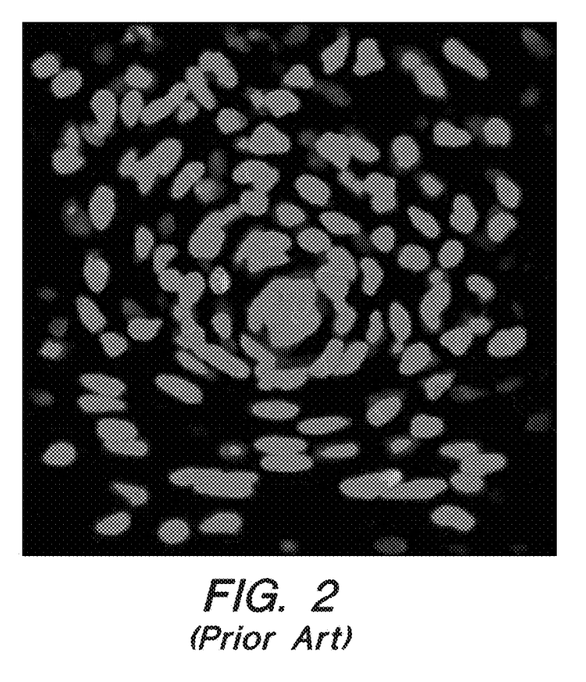
FIG. 2 is a color photograph of the embryo from FIG. 1, after a counting method has been applied.

In the medical/biological fields, cell counting algorithms can be designed to separate somewhat distinct areas. For example, and referring now to prior art FIGS. 1-2, FIG. 1 can be a photograph of a cell assay of CAG::H2B-EGFP Tg/+ E10.5 (an embryonic stem cell from mice) before a blob counting method is applied, while FIG. 2 is a color photograph of the same cell assay after the counting method is applied. From comparing FIG. 1 to FIG. 2, it can be seen that the images are the same (other than a change in color), which can imply that the blob "count" has been accurately captured by the cell counting methods.

Figure 3:
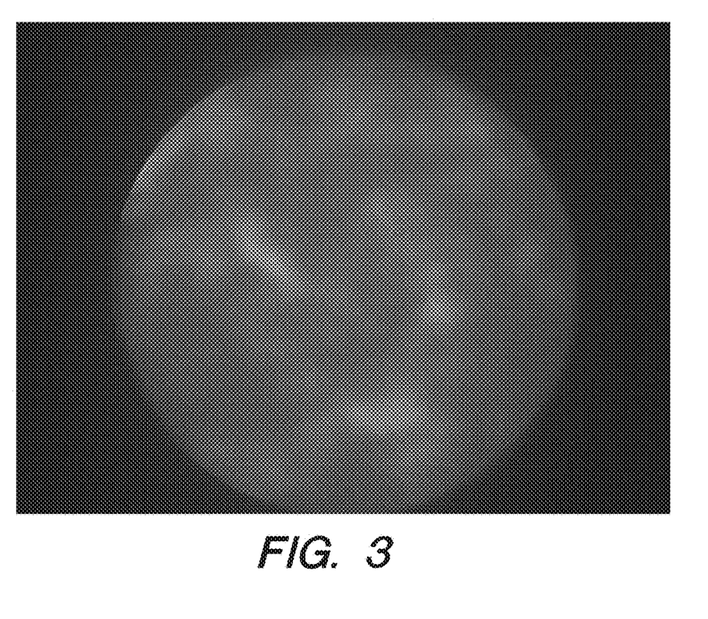
FIG. 3 is a photograph of an image plane of an optical imaging system without preprocessing steps of the present invention according to several embodiments being applied, and prior to the counting method of FIG. 2 being applied.
Figure 4:
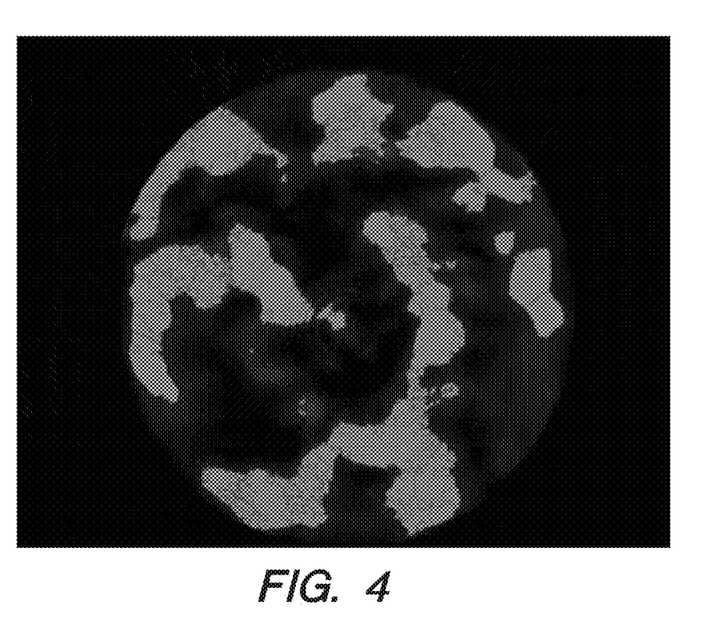
FIG. 4 is the same photograph of FIG. 3, after the counting method of FIG. 2 has been applied.

In contrast, FIGS. 3 and 4 are images of a lens area at a laser communications receiver before and after the same inter-disciplinary cell counting method used in FIG. 2 (the Kostelec method) has been applied. By cross-referencing FIGS. 1-2 and 3-4, it can be seen visually that the cell regions in FIGS. 1-2 are distinct, and can be "counted" much easier. This can be due to a more sharply defined contrast of the cell walls, which can facilitate the methods in distinguishing the blob from the background. On the other hand, and referring to FIGS. 3-4, the turbulent image offers no such help in finding such distinct regions. Furthermore, there are artifacts (reflections, debris, and aberrations of the imaging system) present in the turbulent image which can be misidentified as regions, or which can be incorrectly separated as a single region. From the above, it is clear that the interdisciplinary counting algorithm in its basic form can be unable to correctly separate the turbulent regions and vastly over estimates their number. Thus, in order for a cell counting algorithm from the life sciences to be applied to characterize laser communications in turbulent atmospheres, the image must be preprocessed.

Figure 5:
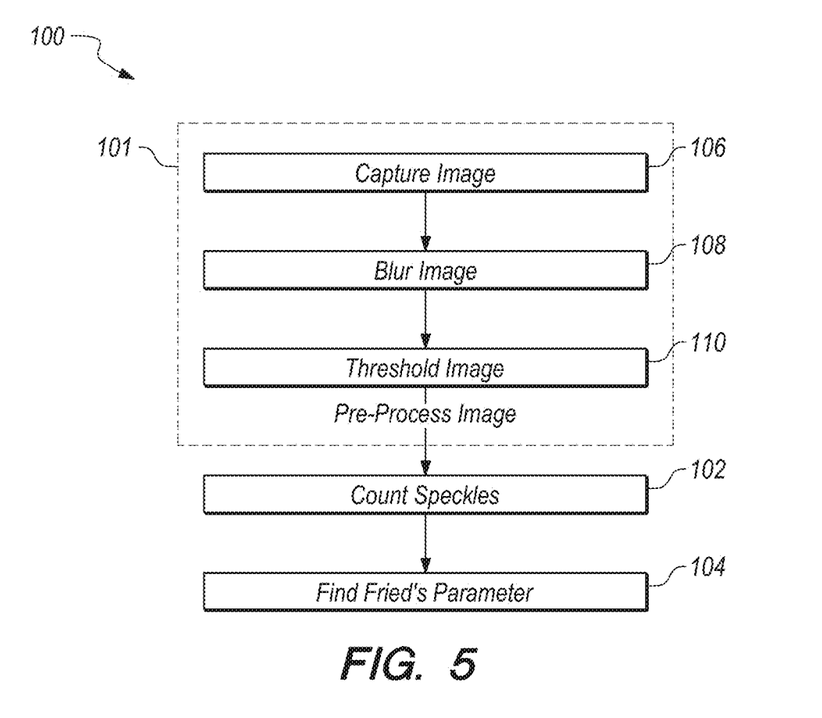
FIG. 5 is a block diagram, which illustrates steps that can be taken to accomplish the methods of the present invention according to several embodiments.

Referring now to FIG. 5, the methods of the present invention according to several embodiments can be depicted by block diagram 100. As shown, method 100 can include the steps of preprocessing the image, as shown by step 101, followed by counting the number of N speckles 102 and finding Fried's parameter $r_0$ using the speckles count N, as illustrated by step 104. The methods can cheaply and effectively characterize atmospheric turbulence without the use of a costly and expensive scintillometer, which can be also be sensitive and difficult to use. But because of the limitations in the lens image discussed above, the lens image must be processed to allow for counting methods to be used to count speckles. Stated differently, the lens image can be preprocessed to allow for speckle counting.

In order to pre-process the image for counting, and as shown in FIG. 5, the image must be captured (step 106) and then blurred (step 108). To accomplish blurring step 108, the images can be passed through a Gaussian blur filter which helps remove the aforementioned artifacts, while retaining the contrast between the speckles, each other, and the background.

Once the image has been blurred, and as shown by step 110 in FIG. 5, the next preprocessing can be thresholding of the image. The thresholding step can limit the pixels from the lens image areas that the algorithm can be used to calculate regions (and determine speckle count). Thresholding enhances the transition from background to turbulent cell, making the image more similar to the analogous cell assays where the cell wall can provide a sharp transition from background to "blob", or cell. As the threshold pixel value for the thresholding step 100 can be increased, the number of regions (speckles) which "make it through" and are counted by the counting algorithm can decrease in both size and number. However, and referring very briefly back to FIGS. 3 and 4, if the threshold level is set too low, the counting algorithm may not be able to distinguish from background, and an inaccurate cell count may result.

Figure 6:
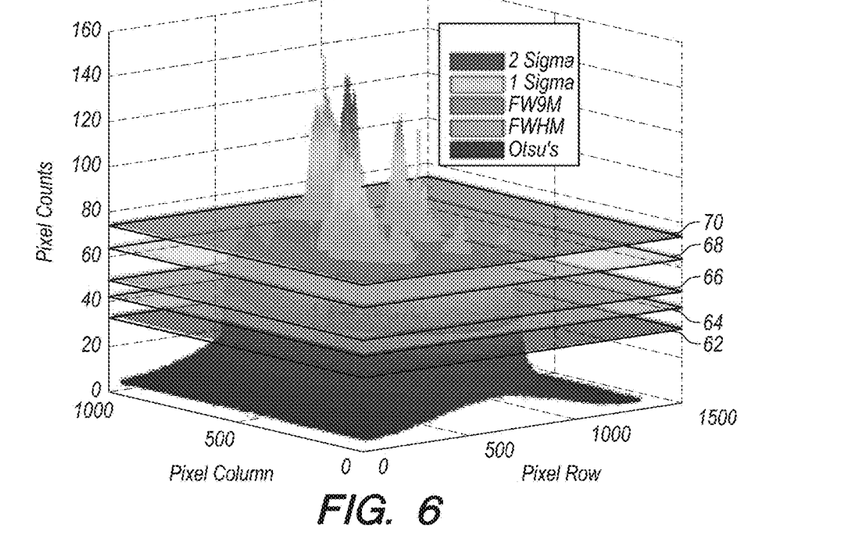
FIG. 6 is a graph of counts that can result using different thresholds when accomplishing the thresholding step using the methods of FIG. 5.
Figure 7:
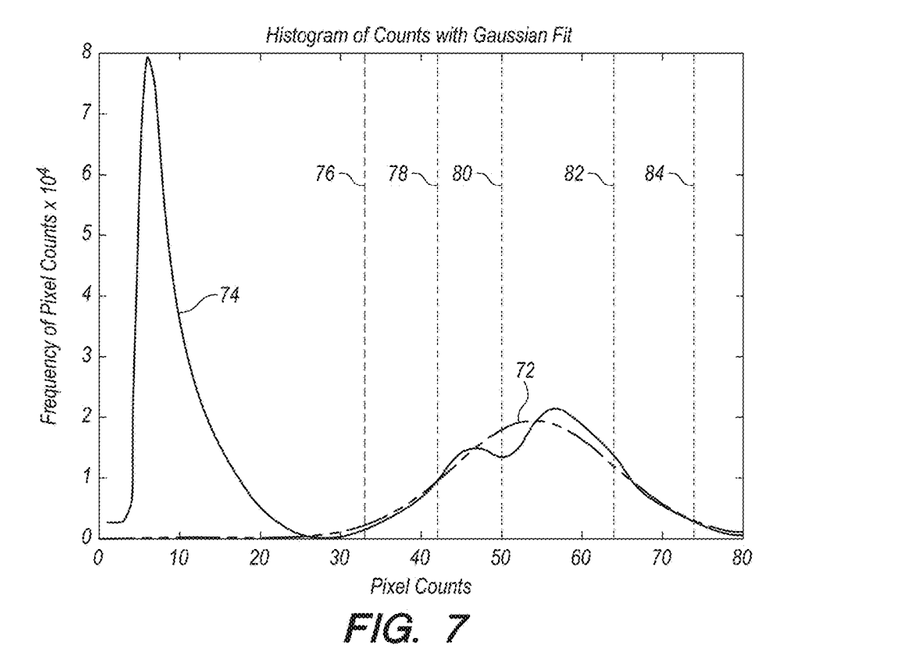
FIG. 7 is a histogram representation of the Gaussian thresholding embodiments of the graph of FIG. 6.

Using the guidelines above, a variety of thresholds can be used. Referring now to FIG. 6, a three-dimensional plot with counts that have result from using different thresholding limits is shown. FIG. 7 is a histograph representation of the Gaussian fits of FIG. 6. The thresholds were chosen by first representing the image as a histogram and allowing only the counts above a certain value to be used in the counting algorithm. From lowest to highest the threshold values were: Ostu's (plane 62); Full Width Half Max (plane 64); Full Width 90% Max (66); 1 Sigma (68); and, 2 Sigma (70). Table 1 lists the algorithms used in FIG. 6.

TABLE 1

| Ostu's | Otsu's method, MATLAB graythresh function, approximately separates foreground from background |
| FWHM | All points above the lower point of the full width half max of the Gaussian fit |
| FW9M | All points above the lower point of the full width 90% max of the Gaussian fit |
| 1 Sigma | All points above +1 sigma point of the Gaussian fit |
| 2 Sigma | All points above +2 sigma point of the Gaussian fit |

Four of the thresholding techniques were using Gaussian statistics. FIG. 7 illustrates a Gaussian curve fit 72 to the image histogram (the large distribution on the left of the plot 74 represents the area outside the circular image as shown in FIG. 7, and the thresholding values can be seen as vertical lines 76-84, corresponding to (in order) Otsu's, FWHM, FW9M, 1 Sigma and 2 Sigma thresholding levels. After experimenting with these thresholding techniques, it can be determined that Ostu's method provided turbulence values appeared to be closest to those measured by scintillometer. However, the other cell thresholding methods could certainly be used. Once an appropriate thresholding method is found the spots can be counted (step 102), and the calculated $r_0$ value can be calculated to describe optical turbulence, but without requiring a scintillometer.

Figure 8:
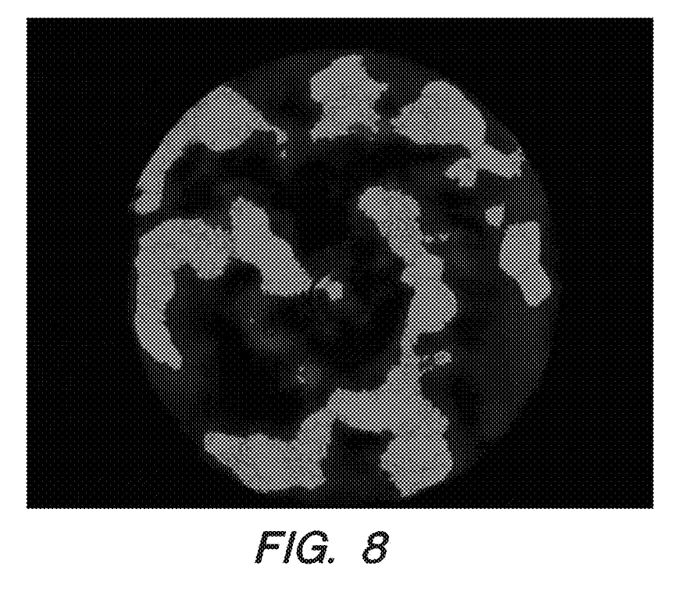
FIG. 8 is the photograph of the same image plane as FIG. 3, but with the preprocessing steps of the methods applied.
Figure 9:
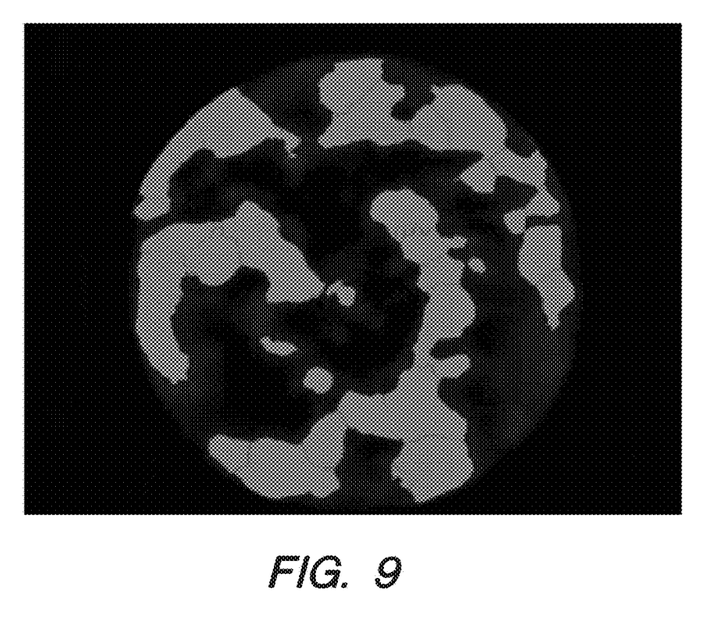
FIG. 9 is the same photograph as FIG. 8, after the counting methods have been applied.

Referring now to FIGS. 8-9. FIG. 8 is a photograph of the same lens image of FIG. 3 after the preprocessing steps described above have occurred. FIG. 9 is a photograph after the same lens image after the Kostelec counting method has been applied. By cross-referencing FIGS. 8-9, and comparing to a cross-referencing of FIGS. 3-4, it can be seen that the preprocessing steps has greatly facilitated the speckle counting. FIGS. 8 and 9 are essentially identical, which means that the count and size of the speckles (if any) that are present is probably accurate. In comparison, from FIGS. 3 and 4 it can be seen that with no preprocessing, the Kostelec method "over counts" speckles that are present. As can be seen from FIGS. 8 and 9, there is a drastic reduction in the number of erroneously counted regions after preprocessing of the images.

D. Data Collection

Figure 10:
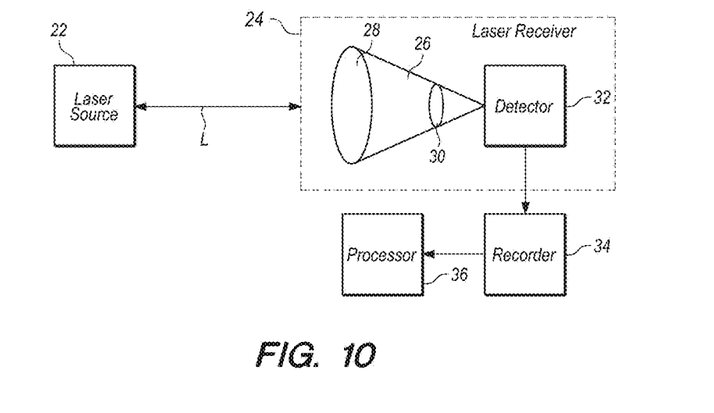
FIG. 10 is a block diagram of the system of the present invention.

Referring now to FIG. 10, a system in according with several embodiments is shown and is generally designated with reference character 20. As shown system 20 can include a laser source 22 and a laser receiver 24. Receiver 24 can include a lens system (telescope 26) with a mask 28 and an imaging lens 30. System 20 can further include a detector 32 and a recorder 34 for recording images. System 20 can also include a processor 36. Processor 36 can include non-transitory instructions for accomplishing the preprocessing sub-steps of the counting step detailed above, as well as finding Fried's number $r_0$.

Telescope 26 can be a 150 mm F/5 (focal range of 5) telescope. Mask 28 can be a 100 mm mask in combination with a 25 mm focal length imaging lens 30. Detector 32 can be a high resolution MAKO GigE camera, manufactured by ALLIED VISION®. Other high resolution cameras could be used. Recorder 36 can use STREAMPIX® (other streaming services could be used), and online video streaming service, to record images. Laser source 22 can be a VSCEL (Vertical Cavity Surface Emitting Laser) array operating at 1064 nm. The array can be a hexagonal package of lasers which can produce a semi-coherent beam. To minimize any possible effects on data collection, laser output beam from source 22 can be routed through a 2 degree diffuser (not shown in FIG. 10). Typically, a diffuser can introduce its own beam speckle but due to the high turbulence during data collection these effects were minimal.

Figure 11:
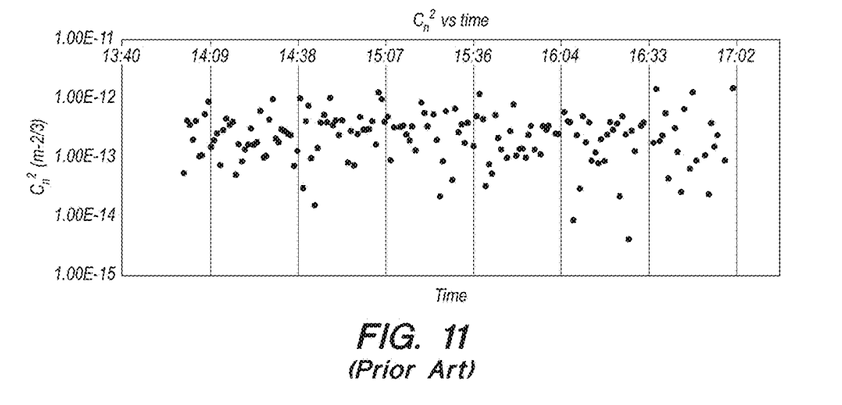
FIG. 11 is a prior art scatter plot of refractive indices, as measured by a scintillometer vice the systems and methods for the present invention.

Operational test data was collected along a laser path with a distance L of one kilometer. Data collection took place on over a three hour period in later afternoon. Within the three hour period, the longest continuous data collection period was over a 5 minute continuous period at 30 frames per second. The exposure on the camera 32 was limited to ~5 ms to prevent oversaturation and smearing of the turbulent images. The images were recorded at recorder 34 and formatted initially in a .seq file format and then exported as .png-formatted images before processing. For Comparison, a BLS900 scintillometer manufactured by Scintech was used to record refractive indices C over the same laser path at 1 minute intervals throughout the same data collection period. These results were plotted as a scatter plot and can be seen in prior art FIG. 11.

E. Analysis and Results

All of the images collected over the 5 minute period were input into the counting algorithm. The above-described preprocessing, Kostelec counting, and Fried determinations steps were accomplished by the processor 36, and the output of the method the number of speckles in each image was recorded. In order to compare to the BLS900 the number of speckles in the image needs to be converted into a $C_n^2$ value, this was achieved by converting the number of speckles into $r_0$ using Equations (2) and (3), and calculating. $C_n^2$ by and rearranging Equation (1) to express the refractive index structure constant in terms of Fried's coherence length, Equation (4):

$$C_n^2 = \frac{r_0^{-\frac{5}{3}}}{1.67k^2 L} \quad (4)$$

Figure 12:
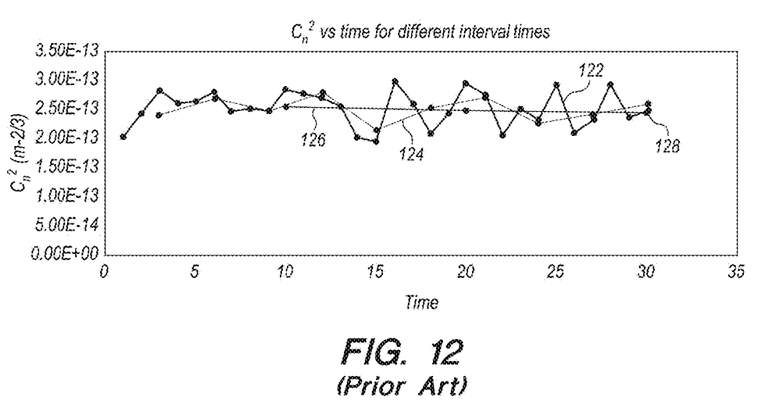
FIG. 12 if a prior art plot of the results of FIG. 11, at various time intervals; and, FIG. 13 is a comparison of the prior art results of FIG. 12 with the systems and methods of the present invention.

Using this process, the $C_n^2$ value for each image was calculated, and then averaged over 1, 3, 10, and 30 second intervals, as shown in FIG. 12. From FIG. 12, it can be seen that shorter averaging intervals offers little extra information and seem to converge to the long scale averaging values. Nevertheless, the 30 second average was used to compare the different thresholding methods and compare against BLS900 data.

Figure 13:
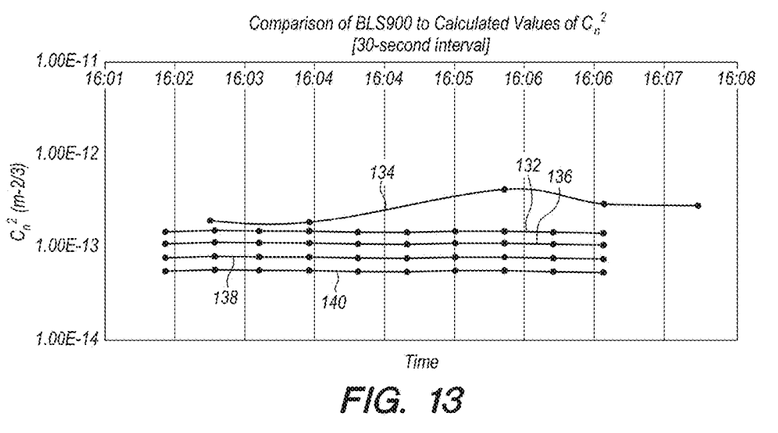

Referring now to FIG. 13, the algorithms are tested on speckle images from experimental data collected over a turbulent 1 km path and compared to $C_n^2$ measurements collected in parallel. Otsu threshold preprocess sub-steps appears result in counts (132 in FIG. 13) that are closest to the BLS900 data (134 in FIG. 13). However, it should be appreciated from FIG. 13 that all of the thresholding methodologies 136-140 result in comparable count results, when compared to scintillometer data 134. Still further, none of the thresholding methods track the trend present in the BLS900 data between 16:04 and 16:06, which was most like caused by discrepancies in optical source, wavelength, averaging time, and path weighting could cause this effect. This could mean that the systems and methods of the present invention can actually avoid some of the sources of error that can be inherent when using a scintillometer.

From the above, it can be seen that the systems and method of the present invention can accomplished very quickly (near-real time) measurement of $r_0$. Additionally, the methods could be compatible with any pupil plane imaging system/camera/wavelength (most scintillometers are designed to operate in a specific wavelength range). The systems and methods could be adapted to incorporate new, future counting methods that may emerge. Still further, changes in hardware (camera, lens diameter, focal length, and wavelength) could result in optimization of counting technique, while an increase in processing speed of processor 36, can speed up the accomplishment of the preprocessing, counting and calculating algorithms described above.

In addition to counting the speckles, the systems and methods can also incorporate the use of speckle size. This can be seen in more detail in a paper entitled "Blob Identification Algorithms Applied to Laser Speckle to Characterize Optical Turbulence" by Galen D. Cauble, et al. The contents of the Cauble paper are hereby incorporated herein by reference The use of the terms "a" and "an" and "the" and similar references in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for characterizing intensity fluctuations as a measure of atmospheric turbulence of free space optical communication of a laser beam, said laser beam being transmitted from a transmitter to a receiver having an image plane, said method comprising the steps of:
   capturing, by a detector, an image that results when said laser beam is incident on said image plane;
   recording, by a recorder, the captured image; and
   performing, by a processor:
   A) preprocessing said captured recorded image from said image plane to limit a number of pixels of said captured recorded image, said preprocessing step resulting in an enhanced preprocessed image;
   B) counting the number of laser speckles at said enhanced preprocessed image from said step A); and,
   C) finding Fried's parameter $r_0$, using the result of said step B), as an indicator of the intensity fluctuations, for measurement of said atmospheric turbulence.

2. The method of claim 1, wherein said step A) further comprises the steps of:
   A1) blurring said captured recorded image; and
   A2) thresholding a pixel count of said blurred image.

3. The method of claim 2, wherein said thresholding step is accomplished using Otsu's method.

4. The method of claim 2 wherein said thresholding step is accomplished by using a Gaussian fit of pixel counts, and then selecting all points above the full width, half max of said Gaussian fit.

5. The method of claim 2 wherein said thresholding step is accomplished by using a Gaussian fit of pixel counts, and then selecting all points above the full width, ninety percent maximum of said Gaussian fit.

6. The method of claim 2 wherein said thresholding step is accomplished by using a Gaussian fit of pixel counts, and then selecting all points above one standard deviation of the mean of the Gaussian fit.

7. The method of claim 2 wherein said thresholding step is accomplished by using a Gaussian fit of pixel counts, and then selecting all points above two standard deviations of the mean of the Gaussian fit.

8. The method of claim 1, wherein said counting step is accomplished using Kostelec's method.

9. The method of claim 1, wherein said counting step is accomplished using Al-Khazraji's method.

10. A method for measuring refractive index fluctuations as a measure of atmospheric turbulence along a laser path of a laser beam, said laser beam being transmitted from a transmitter to a receiver having an image plane, said method comprising the steps of:
    capturing, by a detector, an image that results when said laser beam is incident on said image plane;
    recording, by a recorder, the captured image; and
    performing, by a processor:
    A) preprocessing said captured recorded image from said image plane to limit a number of pixels of said captured recorded image, said preprocessing step resulting in an enhanced recorded image;
    B) counting the number of laser speckles at said enhanced preprocessed image; and,
    C) finding Fried's parameter $r_0$, using the result of said step B as an indicator of the refractive index fluctuations along the path, and further as a measure of said atmospheric turbulence.

11. The method of claim 10, wherein said step A) further comprises the steps of:
    A1) blurring said captured recorded image;
    A2) thresholding a pixel count of said blurred image.

12. The method of claim 11, wherein said thresholding step is accomplished using Otsu's method.

13. The method of claim 11 wherein said thresholding step is accomplished by using a Gaussian fit of pixel counts, and then selecting all points above the full width, half max of said Gaussian fit.

14. The method of claim 11 wherein said thresholding step is accomplished by using a Gaussian fit of pixel counts, and then selecting all points above the full width, ninety percent maximum of said Gaussian fit.

15. The method of claim 11 wherein said thresholding step is accomplished by using a Gaussian fit of pixel counts, and then selecting all points above one standard deviation of the mean of the Gaussian fit.

16. The method of claim 11 wherein said thresholding step is accomplished by using a Gaussian fit of pixel counts, and selecting all points above two standard deviations of the mean of the Gaussian fit.

17. The method of claim 10, wherein said counting step is accomplished using Kostelec's method.

18. The method of claim 10, wherein said counting step is accomplished using Al-Khazraji's method.

19. A system for measuring atmospheric turbulence along a path of a laser beam, comprising:
    a transmitter for transmitting the laser beam along the path;
    a receiver having an image plane;
    a detector for capturing an image that results when said laser beam is incident on said image plane;
    a recorder connected to said receiver for recording said captured image; and,
    a processor connected to said recorder, said processor having non-transitory instructions for preprocessing the captured recorded image to limit a number of pixels of said image from said captured recorded image, to result in an enhanced preprocessed image that only includes said limited number of pixels, and counting the number of speckles in said enhanced preprocessed image, and finding Fried's parameter $r_0$, using the counted number of speckles, as an indicator of the atmospheric turbulence along the path.

20. The system of said claim 19, wherein said processor accomplishes said counting using Kostelec's method.

* * * * *